US006737381B1

(12) United States Patent
Milius et al.

(10) Patent No.: US 6,737,381 B1
(45) Date of Patent: May 18, 2004

(54) PHYTOSANITARY COMPOSITION COMPRISING AT LEAST A WATER SOLUBLE AGENT AND A MODIFIED OIL

(75) Inventors: Alain Milius, Nice (FR); Christian Gauvrit, Dijon (FR); Thomas Muller, Izier (FR); Bernard Brancq, Le Chesnay (FR)

(73) Assignees: Institut National de la Recherche Agronomique, Paris Cedex (FR); Societe d'Exploitation de Produits pour les Industries Chimiques, Paris Cedex (FR)

( * ) Notice: Subject to any disclaimer, the term of this patent is extended or adjusted under 35 U.S.C. 154(b) by 0 days.

(21) Appl. No.: 10/018,885

(22) PCT Filed: May 22, 2000

(86) PCT No.: PCT/FR00/01740

§ 371 (c)(1),
(2), (4) Date: Apr. 4, 2002

(87) PCT Pub. No.: WO01/00028

PCT Pub. Date: Jan. 4, 2001

(30) Foreign Application Priority Data

Jun. 23, 1999 (FR) .......................................... 99 08010

(51) Int. Cl.[7] .......................... A01N 25/30; A01N 57/02
(52) U.S. Cl. ...................... 504/206; 504/362; 514/785; 514/975
(58) Field of Search ................................ 504/206, 362; 514/785, 975

(56) References Cited

U.S. PATENT DOCUMENTS

| 4,557,751 A | | 12/1985 | Ronning et al. ................ 71/91 |
| 4,681,900 A | * | 7/1987 | Iwasaki ...................... 514/786 |
| 6,180,566 B1 | * | 1/2001 | Nielsen et al. .............. 504/206 |
| 6,380,135 B1 | * | 4/2002 | Reuter et al. ................ 504/366 |

FOREIGN PATENT DOCUMENTS

| EP | 0 508 022 | 10/1992 |
| EP | 0 943 241 | 9/1999 |
| FR | 2718980 | 10/1995 |
| FR | 2780612 | 1/2000 |
| HU | 67 542 | 4/1995 |
| WO | WO 92/06596 | 4/1992 |
| WO | WO 96/22109 | 7/1996 |
| WO | WO 96 31121 | 10/1996 |
| WO | WO 99/03343 | 1/1999 |

* cited by examiner

*Primary Examiner*—S. Mark Clardy
(74) *Attorney, Agent, or Firm*—Young & Thompson

(57) ABSTRACT

A phytosanitary treatment method by foliar absorption that uses a composition with at least a water soluble phytosanitary active principle and at least a modified oil, the composition having at least a phytosanitary active principle, at least a vegetable oil and/or an ethoxylated vegetable oil ester.

8 Claims, No Drawings

PHYTOSANITARY COMPOSITION COMPRISING AT LEAST A WATER SOLUBLE AGENT AND A MODIFIED OIL

The invention relates to a method for phytosanitary treatment by foliar absorption, employing a combination between an active principle and a modified oil and a novel combination for employing said method.

The penetration of a phytosanitary active principle into a plant takes place either at leaf level, by foliar absorption, or at root level, by radicular absorption. The foliar absorption of an active principle is often difficult and very slow; this is especially the case for glyphosate which must be formulated with surface-active agents to increase this penetration. In the international patent application published under the number WO 99/03343, the inventors propose the use of methyl esters of ethoxylated fatty it, acids, in combination with vegetable oils, as well as wetting, dispersing and emulsifying agents, in herbicidal concentrations, to improve their stability. However, this approach is not suitable for water-soluble active materials because it leads to emulsions.

However, when small quantities of glyphosate are treated, that is to say of less than or equal to 306 grams per hectare, as is the case in the supervision of fallow land or for the treatment of young annual plants, none of the adjuvants currently employed with this active principle allow a rate of absorption of greater than 50% after 72 hours to be achieved. A period of rain following the treatment of a crop thus risks inducing pollution of the site, while a period of sunshine can cause the degradation of the active principle.

The applicants have thus endeavored to perfect a method of phytosanitary treatment by foliar absorption which allows a high absorption of a hydrophilic active principle by the plant in a short time, while limiting the harm to ecosystems, and using adjuvants which are much less irritant, especially for the eyes, than those used until today.

The invention relates to a method of phytosanitary treatment by foliar absorption, characterised in that it employs an aqueous composition comprising at least one water-soluble phytosanitary active principle and at least one modified oil, chosen from the ethoxylated oils having an ethylene oxide number, called EO index below, of greater than or equal to 20 and less than or equal to 60 and more particularly greater than or equal to 30 and less than or equal to 50 or from ethoxylated methyl, ethyl, linear or branched propyl or linear or branched butyl esters of oils, having an EO index of greater than or equal to 5 and less than or equal to 50 and more particularly greater than or equal to 6 and less than or equal to 20.

The modified oils used in the context of the present invention are of plant origin or of animal origin. Among the modified oils of animal origin which are employed in the method such as is defined above, is, for example, modified tallow oil. Among the modified oils of plant origin which are employed in the method such as defined above, are, for example, in the method sunflower, linseed, soybean, corn, peanut, copra, olive, palm, hydrogenated palm or rapeseed oils.

According to a particular variant of the method, such as defined above, the modified oil comprised in the composition employed is an ethoxylated methyl ester of an oil having an EO index of greater than or equal to 8 and less than or equal to 15.

According to another particular variant of the method, such as defined above, the modified oil comprised in the composition employed is an ethoxylated oil having an EO index of greater than or equal to 30 and less than or equal to 40.

The invention particularly relates to a method such as defined above, for which the modified oil comprised in the composition employed is modified rapeseed oil or modified sunflower oil.

By at least one modified oil, it is indicated that the composition employed in the method which is the subject of the present invention can comprise either a single modified oil, or a mixture of modified oils; in this latter case, it can be a mixture of modified oils of the same origin or a mixture of modified oils of different origins; it can also be a mixture of one or more ethoxylated oils such as are defined above with one or more ethoxylated esters of oils such as are defined above.

Phytosanitary treatment is understood in the context of the present invention as preferably meaning a fungicidal, insecticidal or herbicidal treatment and more particularly a treatment in which the active principle is a compound of chemical structure derived from the radical: $—C(=O)—CH_2—N—CH_2—P(=O)$.

An example of a compound of chemical structure derived from said radical is more particularly glyphosate or N-(phosphonomethyl) glycine, in the form of a water-soluble salt, such as, for example, the monoisopropylamine or trimethylsulfonium salts.

According to another aspect of the present invention, this relates to a composition comprising at least one water-soluble phytosanitary active principle, and at least one modified vegetable oil, characterized in that said modified vegetable oil is chosen from the ethoxylated oils having an ethylene oxide number of greater than or equal to 20 and less than or equal to 60 and more particularly greater than or equal to 30 and less than or equal to 50 or from the ethoxylated methyl, ethyl, linear or branched propyl or linear or branched butyl esters of oils, having an EO index of greater than or equal to 5 and less than or equal to 50 and more particularly greater than or equal to 6 and less than or equal to 20.

In order to improve its behavior in the cold, the alkoxylated oil can be prepared by incorporating, before its alkoxylation, from 1% to 10% by weight of glycerol. This problem is likewise resolved, by combining in the same composition, an alkoxylated vegetable oil such as defined above and an alkoxylated alkyl ester of a vegetable oil such as defined above, and more particularly an ethoxylated methyl, ethyl, linear or branched propyl or linear or branched butyl ester of a vegetable oil.

The invention relates more particularly to a composition, such as defined above, in which the active principle is a compound of chemical structure derived from the radical $—C(=O)—CH_2—N—CH_2—P(=O)$, and is very particularly glyphosate or N-phosphonomethylglycine, in the form of a water-soluble salt, such as, for example, the monoisopropylamine or trimethylsulfonium salts.

The invention relates very particularly to a composition such as defined above, in which the modified oil is an ethoxylated methyl ester of an oil having an EO index of greater than or equal to 8 and less than or equal to 15 and the phytosanitary active principle is glyphosate in the form of a water-soluble salt.

The invention also relates very particularly to a composition such as defined above, in which the modified oil is an ethoxylated oil having an EO index of greater than or equal to 30 and less than or equal to 40 and the phytosanitary active principle is glyphosate in the form of a water-soluble salt.

The invention finally relates very particularly to a composition such as defined above, in which the modified oil is modified rapeseed oil or modified sunflower oil.

EXAMPLE 1

Preparation of Modified Oils

A) Preparation of Ethoxylated Methyl Esters of Rapeseed Oil

The ethoxylated methyl esters of rapeseed oil are obtained from the methyl ester of rapeseed oil by reaction for approximately 45 minutes, at 180° C. and under a pressure of 4.5 bar, with the quantity of ethylene oxide necessary for the obtainment of the desired molar ratio, in the presence of a basic catalyst, then cooling and neutralization of the catalyst.

B) Preparation of Ethoxylated Rapeseed Oils

By employing the method of ethoxylation described in the preceding paragraph, in the presence of 2% by weight of glycerol based on the rapeseed oil, the ethoxylated rapeseed oils are obtained.

EXAMPLE 2

Study of the Capacity of Modified Vegetable Oils to Stimulate the Foliar Penetration of a Phytosanitary Active Principle A) Glyphosate Compositions The penetration into the leaves of barley (Hordeum vulgare 1) of glyphosate, which is a hydrophilic herbicide (log P<−3.4), named N-(phosphonomethyl)glycine, was compared according to the following working method:

Glyphosate labeled with carbon 14 is dissolved in water (4.5 to 21 millimolar; 30 to 50 Bq $\eta L^{-1}$), in the absence of modified vegetable oil. As a reference, the same quantity of radioactive glyphosate is included in a commercial preparation of glyphosate. Ten drops of 0.4 $\eta L$ are applied to the adaxial face of the first barley leaf. At 0, 6, 24 and 72 hours, the product which has not penetrated is washed with 0.5 ml of an acetone/water mixture (1:1, V/V) and the radioactivity is measured by liquid scintillation. The radioactivity present in the treated leaf and in the rest of the plant is determined in the carbon dioxide obtained after combustion of the tissue. The results of three series of analyses which were independent of one another, expressed as the percentage of radioactivity which has penetrated into the plant, with respect to the deposited radioactivity, are shown in the following tables:

TABLE 1

| COMPOSITION | FOLIAR PENETRATION A: | | |
|---|---|---|---|
| | 06 HOURS | 24 HOURS | 72 HOURS |
| Glyphosate + Ethomeen T/25 (1%) | 28% | 39% | 60% |
| Glyphosate + rapeseed oil (6 EO) (1%) | 5% | 25% | 42% |
| Glyphosate + rapeseed oil (10 EO) (1%) | 8% | 30% | 48% |
| Glypyhosate + rapeseed oil (20 EO) (1%) | 18% | 34% | 62% |
| Glyphosate + rapeseed oil (30 EO) (1%) | 28% | 62% | 63% |
| Glyphosate + rapeseed oil (40 EO) (1%) | 34% | 70% | 65% |

The results of this first table demonstrate the superiority of the ethoxylated rapeseed oil, having an EO index of greater than or equal to 20 and especially from 30, as regards the active principle foliar penetration, with respect to that of known additives.

TABLE 2

| COMPOSITION | FOLIAR PENETRATION A: | | |
|---|---|---|---|
| | 06 HOURS | 24 HOURS | 72 HOURS |
| Glyphosate + Ethomeen T/25 (1%) | 32% | 47% | 42% |
| Glyphosate + Methyl ester of rapeseed oil (2 EO) (1%) | 18% | 32% | 30% |
| Glyphosate + Methyl ester of rapeseed oil (3 EO) (1%) | 14% | 28% | 34% |
| Glyphosate + Methyl ester of rapeseed oil (4 EO) (1%) | 14% | 34% | 25% |
| Glyphosate + Methyl ester of rapeseed oil (6 EO) (1%) | 25% | 63% | 63% |
| Glyphosate + Methyl ester of rapeseed oil (8 EO) (1%) | 41% | 60% | 73% |

The results of this second table demonstrate the superiority of ethoxylated methyl esters of rapeseed oil having an EO index of greater than or equal to 6 and more particularly of greater than or equal to 8, as regards the foliar penetration of the active principle, with respect to that of known additives.

TABLE 3

| COMPOSITION | FOLIAR PENETRATION A: | | |
|---|---|---|---|
| | 06 HOURS | 24 HOURS | 72 HOURS |
| Glyphosate + Ethomeen T/25 (1%) | 40% | 50% | 70% |
| Glyphosate + Ethomeen T/25 (1%) + Methyl ester of rapeseed oil (8 EO) (1%) | 60% | 80% | 85% |
| Glyphosate + Ethomeen T/25 (1%) + rapeseed oil (40 EO) (1%) | 49% | 50% | 70% |
| Glyphosate + Ethomeen T/25 (1%) + Methyl ester of rapeseed oil (8 EO) (1%) | 46% | 50% | 74% |
| Glyphosate + rapeseed oil (40 EO) (1%) | 40% | 50% | 70% |

The results of this third table demonstrate the interest that there is in combining one or more modified oils with a hydrophilic active principle for a phytosanitary treatment by foliar absorption.

B) Comparison With the Commercial Formulations of Glyphosate

It has been confirmed that the foliar penetration of the isopropylamine salt of the glyphosate with the methyl ester of rapeseed oil (>8 EO) was more rapid than that of the commercial products based on glyphosate known today, namely round up™, round up™ Bioforce, Ouragan™ or Sting™ ST.

What is claimed is:

1. A method of phytosanitary treatment, characterized in that said method employs an aqueous composition comprising at least one water-soluble phytosanitary active principle and at least one modified oil, chosen from ethoxylated oils having an EO index of greater than or equal to 30 and less than or equal to 40, or from ethoxylated methyl, ethyl, linear or branched propyl or linear or branched butyl esters of oils, having an EO index of greater than or equal to 8 and less than or equal to 15, and wherein said phytosanitary active principle is a compound of chemical structure derived from the radical: —C(=O)—CH$_2$—N—CH$_2$—P(=O), in the form of a water-soluble salt.

2. The method according to claim 1, wherein said aqueous composition comprises at least one or more modified oils of plant origin, selected from the group consisting of modified sunflower, linseed, soybean, corn, peanut, copra, olive, palm, hydrogenated palm and rapeseed oils.

3. The method according to claim 1, wherein said aqueous composition comprises a mixture of a number of modified oils.

4. The method according to claim 1, wherein said modified oil is modified rapeseed oil or modified sunflower oil.

5. A composition comprising at least one water-soluble phytosanitary active principle, and at least one modified vegetable oil, characterized in that said modified vegetable oil is chosen from ethoxylated oils having an ethylene oxide number of greater than or equal to 30 and less than or equal to 40, or from ethoxylated methyl, ethyl, linear or branched propyl or linear or branched butyl esters of oils having an EO index of greater than or equal to 8 and less than or equal to 15, and wherein said phytosanitary active principle is a compound of chemical structure derived from the radical: —C(=O)—CH$_2$—N—CH$_2$—P(=O), in the form of a water-soluble salt.

6. The composition according to claim 5, in which the modified oil of plant origin is selected from the group consisting of modified sunflower, linseed, soybean, corn, peanut, corpra, olive, palm, hydrogenated palm and rapeseed oils.

7. The composition according to claim 5, comprising an alkoxylated vegetable oil and an alkoxylated alkyl ester of a vegetable oil.

8. The composition according to claim 5, in which the modified oil employed is modified rapeseed oil or modified sunflower oil.

* * * * *